(12) United States Patent
Brahney et al.

(10) Patent No.: US 6,990,859 B2
(45) Date of Patent: Jan. 31, 2006

(54) LOCKING MECHANISM FOR LOAD ANALYZER

(75) Inventors: Patrick D. Brahney, Stow, OH (US); Richard J. Macioce, Massillon, OH (US)

(73) Assignee: Bridgestone Firestone North American Tire, LLC, Nashville, TN (US)

( * ) Notice: Subject to any disclaimer, the term of this patent is extended or adjusted under 35 U.S.C. 154(b) by 87 days.

(21) Appl. No.: 10/818,162

(22) Filed: Apr. 5, 2004

(65) Prior Publication Data

US 2005/0217362 A1    Oct. 6, 2005

(51) Int. Cl.
G01M 17/02    (2006.01)
(52) U.S. Cl. ....................................... 73/146
(58) Field of Classification Search ................ 73/146; 425/48; 451/5
See application file for complete search history.

(56) References Cited

U.S. PATENT DOCUMENTS

| | | | | |
|---|---|---|---|---|
| 5,249,460 A | * | 10/1993 | Dory et al. | 73/146 |
| 5,313,827 A | * | 5/1994 | Yovichin | 73/146 |
| 5,347,588 A | * | 9/1994 | Wilson | 382/104 |
| 5,357,799 A | * | 10/1994 | Roth et al. | 73/146 |
| 5,777,219 A | * | 7/1998 | Popio et al. | 73/146 |
| 6,086,452 A | * | 7/2000 | Lipczynski et al. | 451/5 |
| 6,402,491 B1 | * | 6/2002 | Goto | 425/48 |

* cited by examiner

Primary Examiner—Max Noori
Assistant Examiner—Andre Allen
(74) Attorney, Agent, or Firm—James A. Oliff

(57) ABSTRACT

The invention provides a locking mechanism having a catch with a first recess including a lateral wall that extends generally perpendicular to an applied load and an inclined portion that is inclined relative to the lateral wall. The locking mechanism can also include a guide block having a second recess. The guide block can further include a lock wedge that is slidably disposed within the second recess having a first inclined surface that corresponds to the inclined portion of the catch, a second inclined surface, and a contact surface. The guide block can also include a jam wedge that is slidably disposed within the second recess having an inclined surface corresponding to the second inclined surface of the lock wedge. During operation, the lock wedge is urged towards the catch so that a portion of the lock wedge is disposed within the recess of the catch so that the first inclined surface of the lock wedge is in contact with the inclined portion of the catch and the contact surface of the lock wedge is in contact with the lateral wall of the catch. Additionally, the jam wedge can be urged towards the catch so that the inclined surface of the jam wedge is in contact with the second inclined surface of the lock wedge.

23 Claims, 4 Drawing Sheets

UNLOCKED STATE

LOCKED STATE

LOCKING MECHANISM FOR LOAD ANALYZER

BACKGROUND OF THE INVENTION

1. Field of Invention

The invention is related to methods and apparatus for securely locking a test device in place while load related measurements are taken.

2. Description of Related Art

Currently, a radial stiffness contact analyzer (RASCAL) machine can be used to measure performance qualities of a test tire, such as vertical, lateral and fore/aft stiffness. Generally, these tests can be accomplished by either pressing the test tire against a stationary load plate for vertical stiffness measurements, pressing the tire against a movable load plate for lateral and fore/aft stiffness measurement, or holding the test tire stationary while applying a force to a contact surface of the tire via a load plate. As a result of knowing the load or force exerted on the test tire and measuring the resulting deformation of the test tire, a stiffness of the test tire can be determined.

For example, in order to measure fore/aft stiffness of a test tire, the test tire can be mounted on a tire spindle of the radial stiffness contact analyzer. The tire spindle supporting the test tire is then locked in place by a locking assembly so that it will not rotate. Next, a contact surface of the test tire is then brought into contact with a load plate at a predetermined force. The force with which the test tire is brought into contact with the load plate is sufficient to prevent slippage between the test tire and load plate. A force is subsequently applied to the load plate, for example by a hydraulic cylinder or the like, in order to urge the load plate to move under the tire. The force applied to the load plate in turn results in a force being applied to the test tire. The force applied to the test tire also applies a torque or moment about the tire spindle. While the force is being applied, a load cell, linear transducer, or the like, can measure the corresponding deformation of the test tire. Based on these measurements, a stiffness of the test tire can be determined.

Presently, the locking assembly used to lock the tire spindle into place, and thereby to prevent rotation of the tire spindle and test tire, is a pin and sleeve assembly. In such an assembly, the pin is mounted on a stationary housing of the radial stiffness contact analyzer and is used to engage the sleeve mounted on the rotating tire spindle. In other words, the pin is extended to seat within the sleeve, and therefore the tire spindle is no longer able to rotate. Once held in place, the radial stiffness contact analyzer can perform stiffness measurements.

However, a problem with the above-described locking assembly is that the simple pin does not securely engaged the sleeve on the tire spindle, and therefore the tire spindle is able to slightly rotate until the clearances between the pin and sleeve are taken up. This is due in part to the inherent design of the pin and sleeve assembly which require some amount of space or tolerance between the pin and sleeve in order for the pin to be able to move in and out of the sleeve. As a result, there is a problem that the test tire is free to rotate until the clearances are taken up in the locking assembly, which often results in inaccurate stiffness measurements of the test tire.

SUMMARY OF THE INVENTION

The invention can provide a radial stiffness contact analyzer having a stationary portion and a rotating portion on which a tire is mounted. The radial stiffness contact analyzer can include a catch disposed on the rotating portion, the catch having a first recess including an inclined portion and a lateral wall, a guide block disposed on the stationary portion, the guide block including a second recess, a lock wedge that is slidably disposed within the second recess, the lock wedge having a first inclined surface that corresponds to the inclined portion of the catch, a second inclined surface and a contact surface, and a jam wedge that is slidably disposed within the second recess, the jam wedge having an inclined surface corresponding to the second inclined surface of the lock wedge.

In a locked state, the lock wedge can be urged towards the catch so that a portion of the lock wedge is disposed in the recess of the catch so that the first inclined surface of the lock wedge is in contact with the inclined portion of the catch and the contact surface of the lock wedge is in contact with the lateral wall of the catch, and the jam wedge can be urged towards the catch so that the inclined surface of the jam wedge is in contact with the second inclined surface of the lock wedge, thereby restricting the rotation of the rotating portion. Additionally, when the radial stiffness contact analyzer is in an unlocked state, the jam wedge can be urged away from the catch and the lock wedge can also be urged away from the catch so that no portion of the lock wedge is within the recess of the catch.

The radial stiffness contact analyzer described above can further include a first actuator that urges the locked wedge within the second recess of the guide block towards and away from the catch. The radial stiffness contact analyzer can also have a second actuator that urges the jam wedge within the second recess of the guide block towards and away from the catch. The first and second actuators can be at least one of pneumatic, hydraulic and electric type actuators.

In the above-described radial stiffness contact analyzer, the stationary portion can be a housing of the radial stiffness contact analyzer. Further, the rotating portion can be a tire spindle.

The invention can also provide a tire spindle locking apparatus, including a catch having a recess having an inclined surface and a lateral surface, the catch being disposed on the tire spindle, a guide block including a second recess, the guide block being disposed on a stationary housing, and a lock wedge having a first inclined portion and a contact surface, the lock wedge being slidably disposed in the recess of the guide block so that in a locked state a first end of the lock wedge is urged into the recess of the catch so that the first inclined portion of the lock wedge is brought into contact with the inclined surface of the recess and the contact surface of the lock wedge is brought into contact with the lateral wall of the catch.

The tire spindle locking apparatus described above can further include a jam wedge that is slidably disposed within the second recess of the guide block, the jam wedge having an inclined portion that corresponds to a second inclined portion of the lock wedge. In the locked state, the jam wedge also can be urged towards the catch so that the inclined portion of the jam wedge is brought into contact with the second inclined portion of the locked wedge. In an unlocked state, the jam wedge can be urged away from the catch and the lock wedge can also be urged away from the catch so that no portion of the lock wedge is within the recess of the catch.

In the above-describe tire spindle, the catch can be disposed on the tire spindle and the guide block can be disposed on a stationary housing, whereby in the locked state, the tire spindle is not permitted to rotate relative to the stationary housing. Further, the stationary housing can be a radial stiffness contact analyzer.

The invention can provide a locking mechanism, including a catch having a first recess including a lateral wall that extends generally perpendicular to a load and an inclined portion that is inclined relative to the wall, a guide block including a second recess, a lock wedge that is slidably disposed within the second recess, the lock wedge having a first inclined surface that corresponds to the inclined portion of the catch, a second inclined surface, and a contact surface, and a jam wedge that is slidably disposed within the second recess, the jam wedge having an inclined surface corresponding to the second inclined surface of the lock wedge. In a locked state, the lock wedge can be urged towards the catch so that a portion of the lock wedge is disposed within the recess of the catch so that the first inclined surface of the lock wedge is in contact with the inclined portion of the catch and the contact surface of the lock wedge is in contact with the lateral wall of the catch, and the jam wedge can be urged towards the catch so that the inclined surface of the jam wedge is in contact with the second inclined surface of the lock wedge.

Further, in an unlocked state, the jam wedge can be urged away from the catch and the lock wedge can also be urged away from the catch so that no portion of the lock wedge is within the recess of the catch. The catch can be disposed on a rotatable housing and the guide block can be disposed on a stationary housing, whereby in the locked state, the rotatable housing is not permitted to rotate relative to the stationary housing.

BRIEF DESCRIPTION OF THE DRAWINGS

The invention is described with reference to the following figures, wherein like numerals represent like elements, and wherein.

DETAILED DESCRIPTION OF PREFERRED EMBODIMENTS

Figure 1:
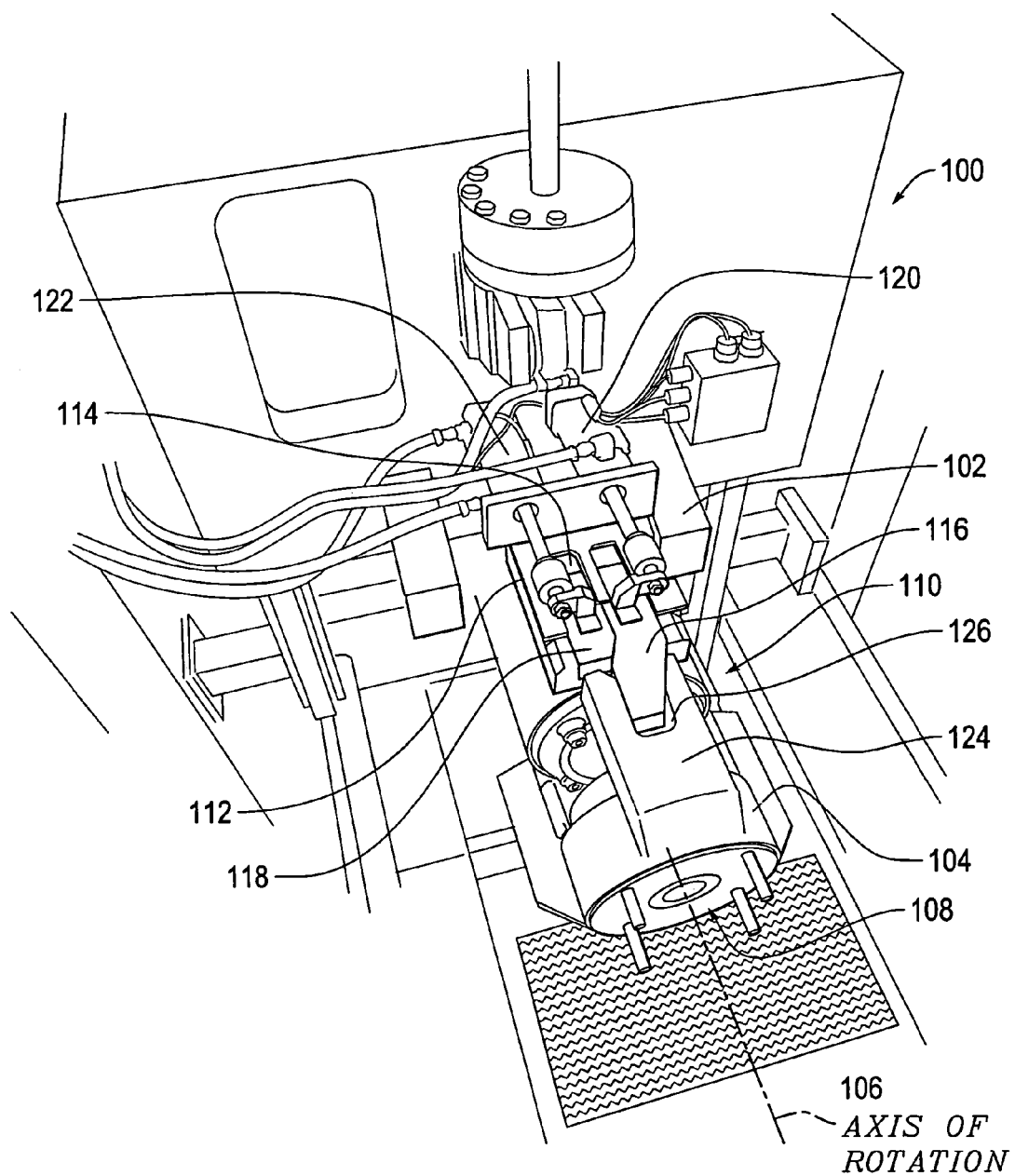
FIG. 1 shows an exemplary radial stiffness contact analyzer machine having a locking mechanism of the present invention.

FIG. 1 shows an exemplary radial stiffness contact analyzer (RASCAL) machine 100 that includes a stationary housing 102 and a rotatable housing 104, such as a tire spindle. The rotatable housing 104 is rotatably mounted to the stationary housing 102 and rotatable about an axis of rotation 106. The rotatable housing 104 can include a tire mount 108 for mounting a test tire (not shown) onto the rotatable housing 104. In order to prevent the rotation of the rotatable housing 104 while performing testing on a test tire, the RASCAL machine 100 further includes a locking mechanism 110. The locking mechanism 110 securely holds the rotatable housing 104 at a particular radial position relative to the stationary housing 102. As shown in FIG. 1, a portion of the locking mechanism 110 is disposed on both the stationary housing 102 and the rotatable housing 104, and generally extends in a direction that is parallel to the axis of rotation 106.

On the stationary housing 102, the locking mechanism 110 includes a guide block 112 having a generally u-shaped recess or opening 114 that extends along the axis of rotation 106 and faces the rotatable housing. The guide block 112 can be mounted to the stationary housing 102 via bolting, welding or the like, or may alternatively be integrally formed as part of the stationary housing 102. The guide block 112 also includes a lock wedge 116 and a jam wedge 118 that are slidably mounted within the u-shaped opening 114 of the guide block 112 to be capable of movement parallel to the axis of rotation 106. While shown as a u-shaped recess, opening 114 can be a recess defined by two generally parallel rails or tracts between which the wedges are disposed.

Further, the stationary housing portion of the locking mechanism 110 includes one or more actuators 120, 122 coupled to the lock wedge 116 and jam wedge 118, respectively, for coordinated movement of the respective wedges 116, 118 between a locked and unlocked position, described in greater detail below. The actuators 120, 122 can be hydraulic, pneumatic, electric or the like. Further, the actuators 120, 122 may be either manually operated or operated under the direction of a controller or control software.

On the rotatable housing 104, the locking mechanism 110 can include one or more catches 124. The catches include a generally u-shaped recess or opening 126 that extends along the axis of rotation 106 and faces the stationary housing 102. As shown, the catches 124 can be integrally formed as part of the rotatable housing 104, or may alternatively be mounted on the rotatable housing 104 by bolting, welding or the like. While shown as a u-shaped recess, opening 126 can be a recess defined by two rails or tracts.

Figure 2:
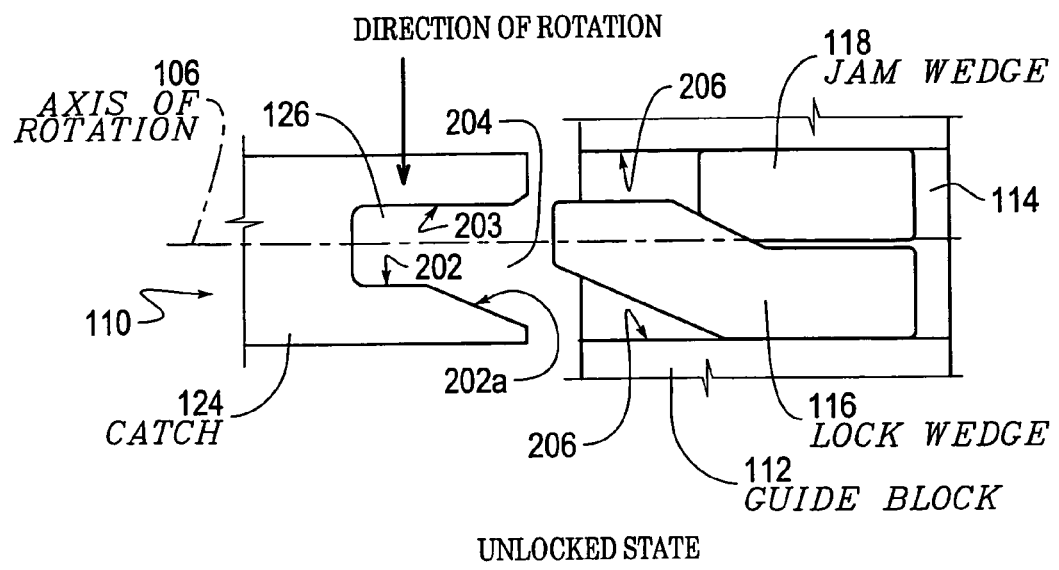
FIG. 2 is a plan view showing an exemplary embodiment of the present invention in an unlocked state.

Referring to FIG. 2, there is shown a plan view of the locking mechanism 110 in an unlocked state. As shown, the catch 124 includes the generally u-shaped recess 126. During operation, the recess 126 is designed to receive the lock wedge 116 in order to prevent radial movement of the rotatable housing 104. FIG. 2 shows a direction of rotation of the rotatable housing 104. As shown in this example, the lateral walls 202 and 203 of the recess 126 generally extend along a direction parallel to the axis of rotation 106. More specifically, lateral wall 203 extends in a direction that is perpendicular to a direction of force or load. For example, as shown in FIG. 2, the catch 124 is mounted on the rotatable housing 104 that is being urged to rotate in the direction of rotation shown in that figure. Accordingly, the lateral wall 203 extends in a direction perpendicular to the direction of rotation (i.e., parallel to the axis of rotation 106). Further, the lateral wall 202 includes an inclined portion 202a that is inclined away from the lateral wall 203. As shown, the inclined portion 202a can extend from a position on the lateral wall 202 to an opening 204 of the recess 126.

FIG. 2 also shows a plan view of the guide block 112 including the lock wedge 116 and the jam wedge 118. As shown, the guide block 112 includes the generally u-shaped recess 114 with lateral walls 206 of the recess 114 extending in a direction generally parallel to the axis of rotation 106. Accordingly, the lateral walls 206 form a channel for the lock and jam wedges. As described above, both the lock wedge 116 and jam wedge 118 are slidably mounted within the recess 114 of the guide block 112 for movement in a direction parallel to the axis of rotation.

Figure 3:
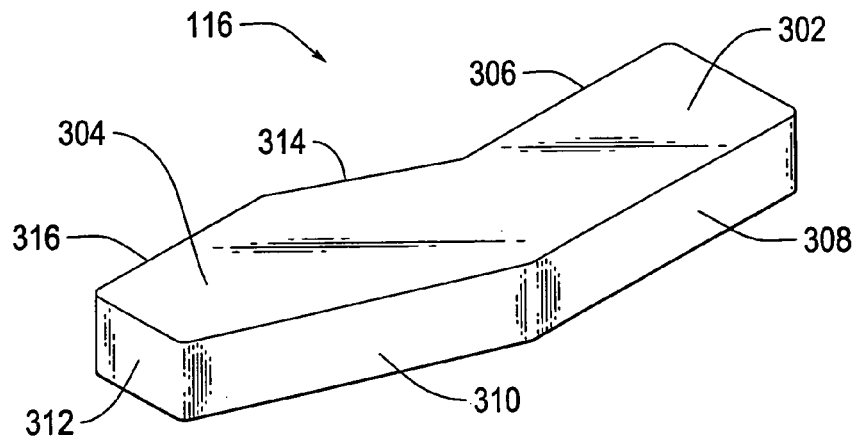
FIG. 3 is a view showing an exemplary embodiment of the lock wedge of the present invention.

As shown in FIG. 3, the lock wedge 116 is an elongated member having a guide block portion 302 and a catch engaging portion 304. The guide block portion 302 includes parallel walls 306, 308 that extend in a direction that is generally parallel to the axis of rotation 106. As shown in FIG. 2, the wall 306 is adjacent to and in contact with the jam wedge 118, while the wall 308 is adjacent to and in contact with the wall 206 of the guide block 112. Thus, the lock wedge 116 is free to travel in a direction generally parallel to the axis of rotation 106 within the guide block 112.

Referring back to FIG. 3, the catch engaging portion 304 of the lock wedge 116 includes a first inclined surface 310 that extends from the wall 308 to a tip 312 of the lock wedge 116. As described in greater detail below, the first inclined surface 310 is inclined so as to correspond to and mate with the inclined portion 202*a* of the catch 124.

The catch engaging portion 302 also includes a second inclined surface 314 that extends from the wall 306 to a contact portion 316. The contact portion 316 extends from the second inclined surface 314 of the tip 312 and, as described in greater detail below, is designed to engage the wall 203 of the catch 124 to prevent rotation. While the second inclined surface 314 is shown as generally parallel to the first inclined surface 310, it should be understood that this is not necessary, and the inclined surfaces 310 and 314 can be inclined at different angles.

Figure 4:
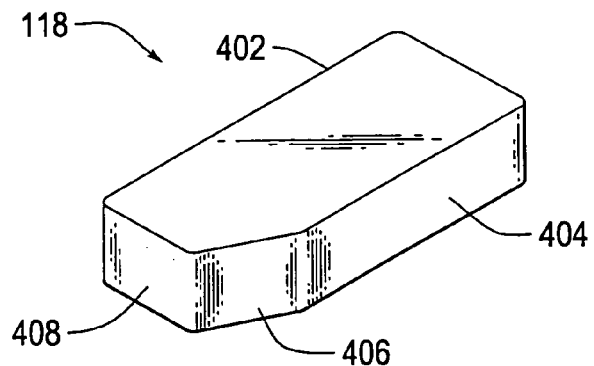
FIG. 4 is a view showing an exemplary embodiment of the jam wedge of the present invention.

Referring now to FIG. 4, the jam wedge 118 is an elongated member having parallel walls 402 and 404 that extend in a direction that is generally parallel to the axis of rotation 106. As shown in FIG. 2, the wall 404 is adjacent to and in contact with the lock wedge 116, while the wall 402 is adjacent to and in contact with the guide block 112. The jam wedge 118 further includes an inclined portion 406 that extends from the wall 404 to a tip 408. The inclination or angle of the inclined portion 406 of the jam wedge 118 corresponds to the inclination or angle of the second inclined surface 314 of the lock wedge 116 so that the two parts can slidably engage each other, as described in greater detail below.

Referring back to FIG. 2, there is shown the locking mechanism 110 in an unlocked state, whereby the rotatable housing 104 is free to rotate about the axis of rotation 106. As shown, in the unlocked state, both the lock wedge 116 of the jam wedge 118 are at least partially retracted into the recess 114 and away from the catch 124, and therefore do not engage the catch 124. Accordingly, the rotatable housing 104 on which the catch 124 is mounted is free to rotate about its axis since its rotation is unobstructed.

Figure 5:
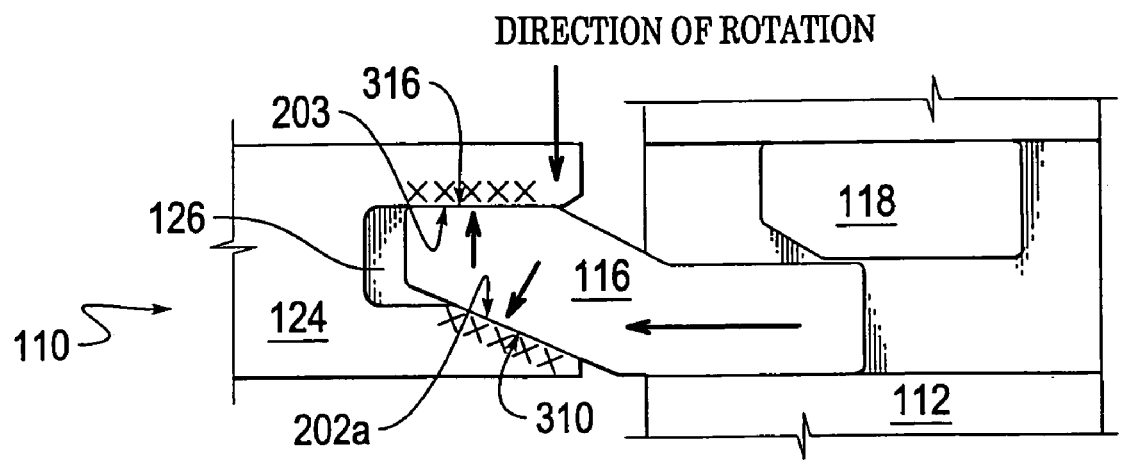
FIG. 5 is a plan view showing an intermediate locking state of the locking mechanism of the present invention.

FIG. 5 shows an intermediate state of the locking mechanism 110. As shown, the catch 124 and the guide block 112 are roughly aligned with each other and the lock wedge 116 is slid toward the catch 124 along a direction parallel to the axis of rotation 106 so that the contact portion 316 and the first inclined surface 310 are in contact with the lateral wall 203 and inclined portion 202*a*, respectively, of the catch 124. Accordingly, the contact surface 316 of the lock wedge 116 is urged against the wall 203 of the catch 124 and cinched tightly within the catch recess 126. In other words, by virtue of the force exerted on the first inclined surface 310 by the inclined portion 202*a*, lock wedge 116 is urged away from the inclined portion 202*a*, and thereby forcing contact surface 316 into contact with wall 203. At this intermediate state, the position of the jam wedge 118 remains unchanged from the unlock state shown in FIG. 2.

Figure 6:
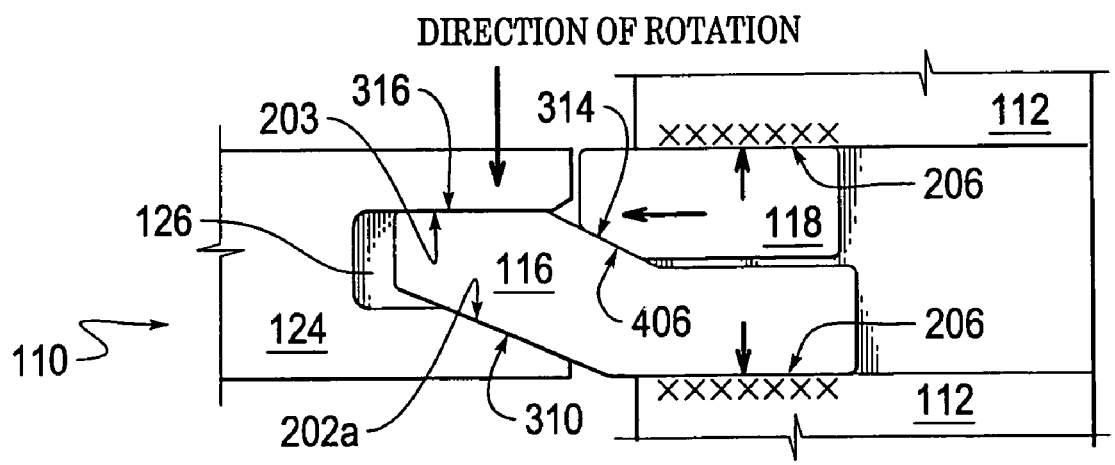
FIG. 6 is a plan view showing an exemplary embodiment of the locking mechanism of the present invention in a locked state.
Figure 7A:
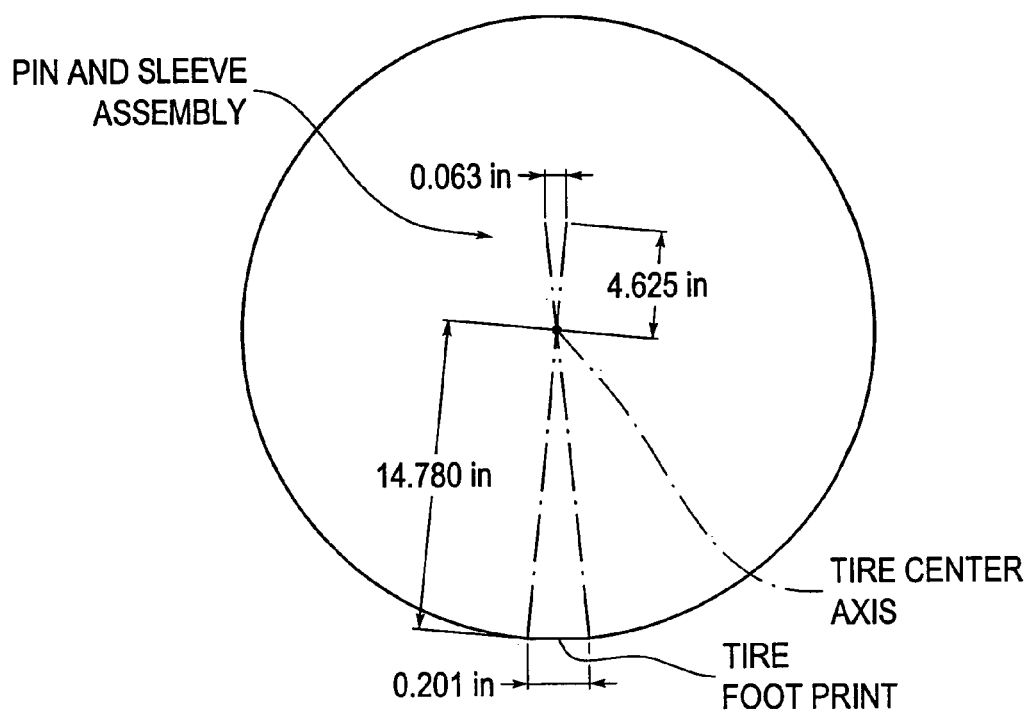
FIGS. 7a and 7b are exemplary graphical representations showing test measurements made using prior locking assemblies and the present locking mechanism, respectively.
Figure 7B:
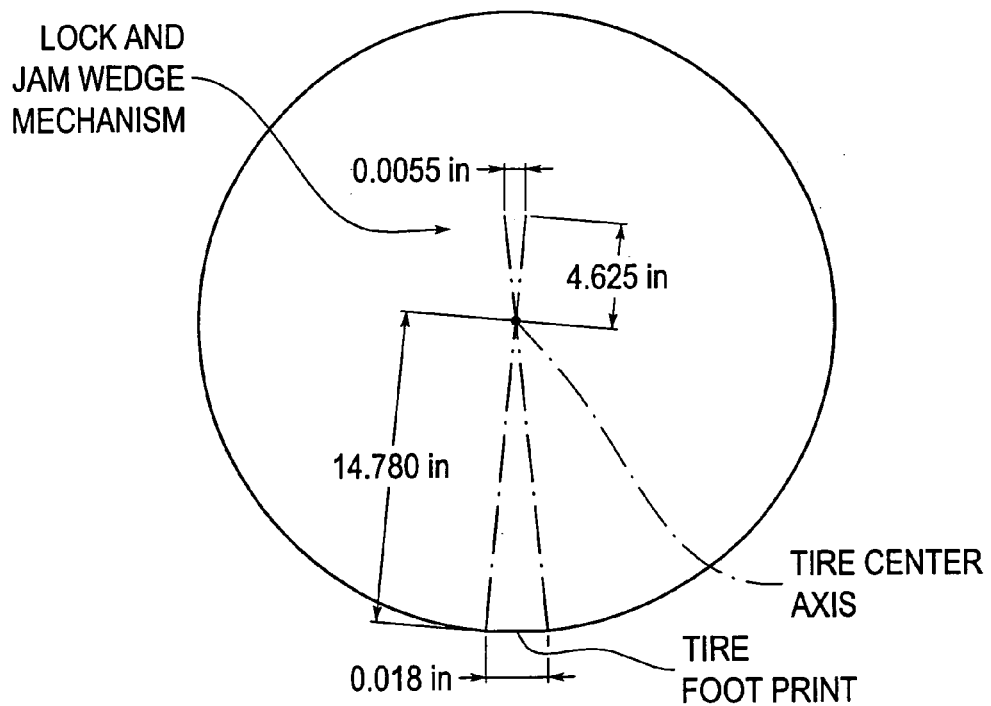

FIG. 6 shows a locked state of the locking mechanism 110. As shown, the jam wedge 118 is moved towards the catch 124 in a direction that is generally parallel to the axis of rotation 106, so that the inclined part 406 is brought into contact with the second inclined surface 314. The jam wedge 118 is urged against the lock wedge 116 with sufficient force to cause both the jam wedge 118 and the lock wedge 116 to be cinched within the walls 206 of the guide block 112. In other words, by virtue of the force exerted on the second inclined surface 314 of the lock wedge 116 by the first inclined portion 406 of the jam wedge 118, the lock and jam wedges are urged apart from one another. As a result of being urged apart, the lock and jam wedges are forced into contact with the walls 206 of the guide block 112, and thereby cinched securely in place.

In the locked state shown in FIG. 6, the contact portion 316 is firmly secured against the wall of the catch 124 by virtue of the force exerted by the inclined surfaces 202*a* and 310. As can be seen, because of the tapered nature of the lock wedge 116, there is no tolerance or play that needs to be taken up, as with the prior pin and sleeve assembly. In other words, because the lock wedge 116 fits securely in the recess 126 of the catch 124 there is no space or tolerance to be taken up. Further, if the surfaces 202*a*, 203, 310 or 316 should become worn, the design will automatically account for such where by inserting the lock wedge 116 further into the recess 126 of the catch 124.

Referring now to FIGS. 6*a* and 6*b*, there is shown a graphical representation of the improvement in performance provided by the invention. FIG. 6*a* shows an example using the prior pin and sleeve locking assembly. The figure shows an amount of movement or rotation that the pin and sleeve locking assembly permit about a tire center axis, as well as the movement of the test tire contact surface in a lateral direction at the tire footprint that results from the rotation. As shown in this example, the tolerances in the pin and sleeve assembly permit 0.063 inches of movement at the locking assembly which translates into 0.201 inches of movement at the tire footprint. The difference in movement being directly related to the distances of the locking assembly and contact surface from the tire center axis. In other words, small movements at the locking assembly result in greater movement at the tire footprint.

FIG. 6*b* shows an example where the locking mechanism, having the lock and jam wedges, is used to secure the tire spindle. In this example, the locking mechanism only permits 0.0055 inches of movement at the locking assembly which translates to 0.018 inches of movement at the tire footprint. As described above, the reduction of movement at the tire footprint results in a more accurate stiffness measurement of the test tire.

As described above, the invention can provide a locking device that is capable of rapidly locking the tire spindle to the housing in such a manner as to have no clearance between the mating parts in a locked state, thus resulting in accurate stiffness measurements of the test tire. In other words, once the locking mechanism of the present invention is engaged, the tire spindle will not rotate and the radial stiffness contact analyzer will be able to take accurate measurements of the test tire.

As also described above, a problem with the prior locking assemblies is that the tolerances with which the locking pin is received in the sleeve result in a small amount of slippage between the tire spindle and stationary housing. In other words, in order for the pin to be freely inserted into the sleeve, a diameter of the pin must be slightly less than an inner diameter of the sleeve. Accordingly, there is an inherent play in the movement between the pin and sleeve. As a result, and usually during an initial stage of the measurement process, the test tire is permitted to slightly rotate until this tolerance is taken up. As described above, this undesired rotation results in an inaccurate tire stiffness measurement.

In addition to the inherent play within the pin and sleeve design, extended use of the pin and sleeve can increase such movement, and therefore increase the inaccuracy of the radial stiffness contact analyzer. In other words, normal wear and tear upon either the pin or the sleeve as a result of use can result in additional space between the pin and internal walls of the sleeve. As a result, even greater inaccuracy in measurements can occur.

The inclined portions of the catch, lock wedge and jam wedge of the invention can eliminate the clearances between the pin and sleeve that is present in the current locking assemblies. Furthermore, as a result of its inclined design, the invention can self adjust for wear since tolerances resulting from wear are cinched up by simply urging the lock or jam wedges further towards the catch.

Further, as a result of the inclined mating surfaces of the lug and catch of the invention, once the lock is engaged, the tire spindle is securely held stationary with no clearance between engaged members at the lock position. Therefore, the invention can result in more accurate stiffness measurements of a test tire since the tire spindle is securely locked in place during the entire measurement.

While the invention has been described with reference to preferred embodiments, it should be understood that various changes can be made without departing from the spirit and scope of the present invention. For example, while the preferred embodiment is given in the context of a radial stiffness contact analyzer, it should be understood that the locking mechanism can be applied to other devices that require a secure engagement to prevent relative movement. Additionally, while the preferred embodiment has been described to prevent radial movement of a rotatable part relative to a stationary part, it should be understood that the locking mechanism can also prevent lateral movement between a stationary part and a laterally moveable part.

Accordingly, while this invention has been described in conjunction with the specific embodiments, it is evident that many alternatives, modifications and variations will be apparent to those skilled in the art. Accordingly, preferred embodiments of the invention as set forth herein are intended to be illustrative, not limiting. Various changes may be made without departing from the spirit and scope of the invention.

What is claimed is:

1. A radial stiffness contact analyzer having a stationary portion and a rotating portion on which a tire is mounted, the radial stiffness contact analyzer comprising:
   a catch disposed on the rotating portion, the catch having a first recess including an inclined portion and a lateral wall;
   a guide block disposed on the stationary portion, the guide block including a second recess;
   a lock wedge that is slidably disposed within the second recess, the lock wedge having a first inclined surface that corresponds to the inclined portion of the catch, a second inclined surface and a contact surface;
   a jam wedge that is slidably disposed within the second recess, the jam wedge having an inclined surface corresponding to the second inclined surface of the lock wedge; and
   wherein, in a locked state, the lock wedge is urged towards the catch so that a portion of the lock wedge is disposed in the recess of the catch so that the first inclined surface of the lock wedge is in contact with the inclined portion of the catch and the contact surface of the lock wedge is in contact with the lateral wall of the catch, and the jam wedge is urged towards the catch so that the inclined surface of the jam wedge is in contact with the second inclined surface of the lock wedge, thereby restricting the rotation of the rotating portion.

2. The radial stiffness contact analyzer of claim 1, wherein in an unlocked state, the jam wedge is urged away from the catch and the lock wedge is also urged away from the catch so that no portion of the lock wedge is within the recess of the catch.

3. The radial stiffness contact analyzer of claim 1, further comprising a first actuator that urges the locked wedge within the second recess of the guide block towards and away from the catch.

4. The radial stiffness contact analyzer of claim 3, further comprising a second actuator that urges the jam wedge within the second recess of the guide block towards and away from the catch.

5. The radial stiffness contact analyzer of claim 4, wherein the first and second actuators are at least one of pneumatic, hydraulic and electric type actuators.

6. The radial stiffness contact analyzer according to claim 1, wherein the stationary portion is a housing of the radial stiffness contact analyzer.

7. The radial stiffness contact analyzer according to claim 1, wherein the rotating portion is a tire spindle.

8. A tire spindle locking apparatus, comprising:
   a catch including a recess having an inclined surface and a lateral surface, the catch being disposed on the tire spindle;
   a guide block including a second recess, the guide block being disposed on a stationary housing; and
   a lock wedge having a first inclined portion and a contact surface, the lock wedge being slidably disposed in the recess of the guide block so that in a locked state a first end of the lock wedge is urged into the recess of the catch so that the first inclined portion of the lock wedge is brought into contact with the inclined surface of the recess and the contact surface of the lock wedge is brought into contact with the lateral wall of the catch.

9. The tire spindle locking apparatus according to claim 8, further comprising a jam wedge that is slidably disposed within the second recess of the guide block, the jam wedge having an inclined portion that corresponds to a second inclined portion of the lock wedge.

10. The tire spindle according to claim 9, wherein in the locked state, the jam wedge also is urged towards the catch so that the inclined portion of the jam wedge is brought into contact with the second inclined portion of the locked wedge.

11. The tire spindle of claim 10, wherein in an unlocked state, the jam wedge is urged away from the catch and the lock wedge is also urged away from the catch so that no portion of the lock wedge is within the recess of the catch.

12. The tire spindle of claim 11, further comprising a first actuator for urging the locked wedge within the second recess of the guide block towards and away from the catch.

13. The tire spindle of claim 12, further comprising a second actuator for urging the jam wedge within the second recess of the guide block towards and away from the catch.

14. The tire spindle of claim 13, wherein the first and second actuators are at least one of pneumatic, hydraulic and electric type actuators.

15. The tire spindle according to claim 8, wherein the catch is disposed on the tire spindle and the guide block is disposed on a stationary housing, whereby in the locked state, the tire spindle is not permitted to rotate relative to the stationary housing.

16. The tire spindle according to claim 15, wherein the stationary housing is a radial stiffness contact analyzer.

17. A locking mechanism, comprising:
- a catch having a first recess including a lateral wall that extends generally perpendicular to a load and an inclined portion that is inclined relative to the wall;
- a guide block including a second recess;
- a lock wedge that is slidably disposed within the second recess, the lock wedge having a first inclined surface that corresponds to the inclined portion of the catch, a second inclined surface, and a contact surface;
- a jam wedge that is slidably disposed within the second recess, the jam wedge having an inclined surface corresponding to the second inclined surface of the lock wedge; and
- wherein, in a locked state, the lock wedge is urged towards the catch so that a portion of the lock wedge is disposed within the recess of the catch so that the first inclined surface of the lock wedge is in contact with the inclined portion of the catch and the contact surface of the lock wedge is in contact with the lateral wall of the catch, and the jam wedge is urged towards the catch so that the inclined surface of the jam wedge is in contact with the second inclined surface of the lock wedge.

18. The locking mechanism of claim 17, wherein in an unlocked state, the jam wedge is urged away from the catch and the lock wedge is also urged away from the catch so that no portion of the lock wedge is within the recess of the catch.

19. The locking mechanism of claim 17, further comprising a first actuator that urges the locked wedge within the second recess of the guide block towards and away from the catch.

20. The locking mechanism of claim 19, further comprising a second actuator that urges the jam wedge within the second recess of the guide block towards and away from the catch.

21. The locking mechanism of claim 20, wherein the first and second actuators are at least one of pneumatic, hydraulic and electric type actuators.

22. The locking mechanism according to claim 17, wherein the catch is disposed on a rotatable housing and the guide block is disposed on a stationary housing, whereby in the locked state, the rotatable housing is not permitted to rotate relative to the stationary housing.

23. The locking mechanism according to claim 22, wherein the rotatable housing is a tire spindle.

* * * * *